(12) United States Patent
Muto et al.

(10) Patent No.: US 7,626,029 B2
(45) Date of Patent: Dec. 1, 2009

(54) METHOD OF SELECTIVELY INTRODUCING AMINO SUBSTITUENT

(75) Inventors: Makoto Muto, Tokyo (JP); Yutaka Kitagawa, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 627 days.

(21) Appl. No.: 10/560,823

(22) PCT Filed: Jun. 18, 2004

(86) PCT No.: PCT/JP2004/008607

§ 371 (c)(1),
(2), (4) Date: Dec. 15, 2005

(87) PCT Pub. No.: WO2004/113321

PCT Pub. Date: Dec. 29, 2004

(65) Prior Publication Data

US 2006/0122396 A1 Jun. 8, 2006

(30) Foreign Application Priority Data

Jun. 19, 2003 (JP) ............................. 2003-175212

(51) Int. Cl.
*C07D 215/38* (2006.01)
(52) U.S. Cl. ...................................... 546/157; 546/159
(58) Field of Classification Search ................. 546/157, 546/159
See application file for complete search history.

(56) References Cited

U.S. PATENT DOCUMENTS

| 5,849,757 | A | 12/1998 | Takemura et al. |
| 2004/0063754 | A1 | 4/2004 | Takahashi et al. |
| 2005/0143407 | A1 | 6/2005 | Ohta et al. |
| 2006/0122396 | A1 | 6/2006 | Muto et al. |
| 2007/0123560 | A1 | 5/2007 | Takahashi et al. |

FOREIGN PATENT DOCUMENTS

| EP | 0 882 725 A1 | 12/1998 |
| EP | 1 336 611 A1 | 8/2003 |
| WO | 96/23782 | * 2/1996 |
| WO | 97/19072 | * 11/1996 |
| WO | 97/19072 | 5/1997 |
| WO | 02/40487 | * 5/2002 |

OTHER PUBLICATIONS

U.S. Appl. No. 10/559,499, filed Dec. 5, 2005, Muto, et al.

* cited by examiner

*Primary Examiner*—D. Margaret Seaman
(74) *Attorney, Agent, or Firm*—Oblon, Spivak, McClelland, Maier & Neustadt, L.L.P.

(57) ABSTRACT

Provided are a technique for position-selectively introducing an amino group into a difluorobenzoic acid, a novel process for producing a quinolonecarboxylic acid derivative serving as an antibacterial agent, and intermediates in the production. The process comprises treating a compound represented by formula (6):

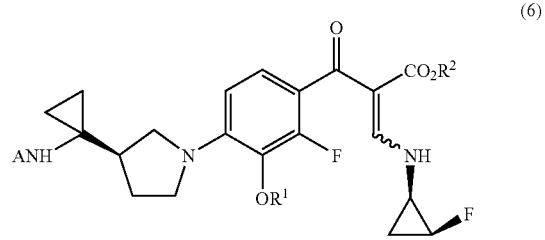

(6)

with a base in a water-containing solvent. The intermediates are represented by formula (6):

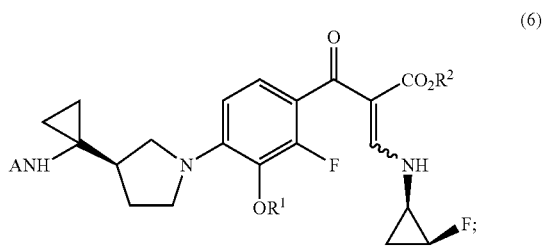

(6)

formula (5):

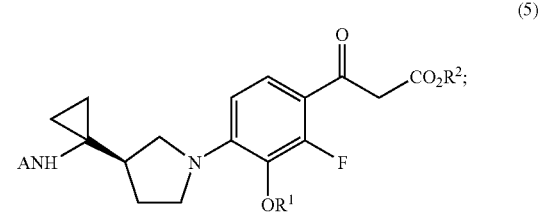

(5)

formula (4):

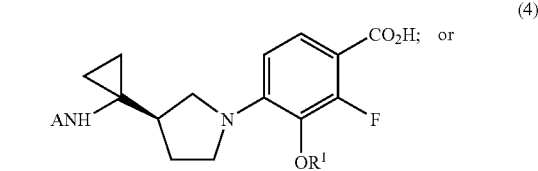

(4)

formula (3):

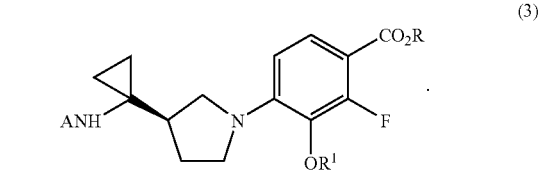

(3)

8 Claims, No Drawings

METHOD OF SELECTIVELY INTRODUCING AMINO SUBSTITUENT

TECHNICAL FIELD

The present invention relates to a method for producing a quinolonecarboxylic acid which is a synthetic antibacterial agent and is highly promising as an excellent medicament, an agricultural chemical or a veterinary drug, as well as novel intermediates in the production thereof.

BACKGROUND ART

Quinolonecarboxylic acid derivatives are widely used for medical purpose as a synthetic antibacterial agent. However, emergence of resistant bacteria represented by MRSA has become a major obstacle in such treatment. The quinolonecarboxylic acid derivative represented by formula (1'):

(1')

not only exhibits excellent effects on MRSA but also exhibits an antibacterial activity against resistant gram-positive bacteria, and thus is a compound which can solve problems associated with various resistant bacteria. As a process for producing the compound is known a process shown by the following reaction scheme (for example, see Patent Document 1):

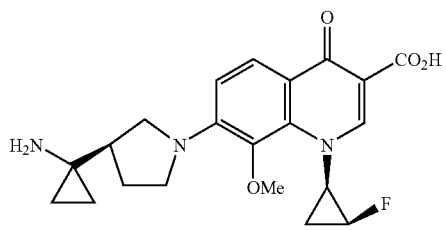

(X = Cl)

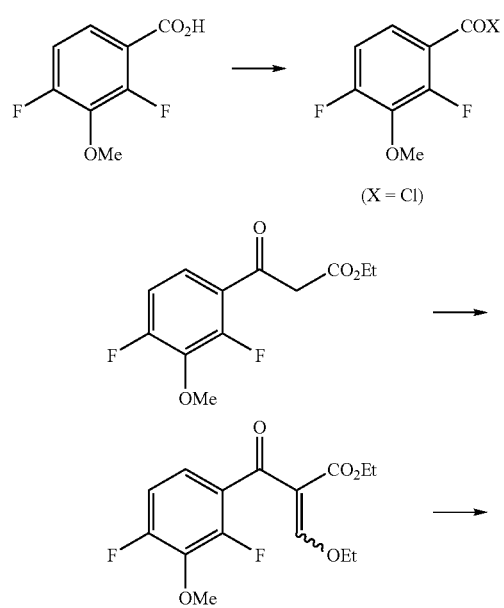

Patent Document 1: International Publication WO 02/040478 gazette

DISCLOSURE OF THE INVENTION

Problems to be Solved by the Invention

Hitherto, there has not been a technique for position-selectively introducing an amino group into difluorobenzoic acids. Thus it has been conducted to introduce an amino group into a quinolone mother nucleus at 7-position after producing the mother nucleus. According to a conventional process, however, expensive (1R,2S)-2-fluorocyclopropylamine tosylate is used at an earlier step in the production of the mother nucleus, thereby providing a problem of high production cost.

Accordingly, an object of the present invention is to develop a technique for position-selectively introducing an amino group into difluorobenzoic acids to provide a novel process for producing a quinolone and intermediates produced in the process.

Means to Solve the Problem

The present inventors have made extensive research and have found that it is possible to position-selectively control the reaction of introducing an amino substituent, particularly a cyclic amino substituent, into a 2,4-difluoro-3-alkoxybenzoate by selecting a reaction solvent. For the production of a compound which is necessary for producing a quinolone compound, in which an amino substituent is introduced at 4-position, such as a compound of formula (3) shown below, use of dimethylsulfoxide as a reaction solvent is most effective. By producing selectively a compound in which an amino substituent is introduced at 4-position and using the compound as a key intermediate, a novel process for producing a quinolone has been completed. An example of the process of the present invention is shown by way of the following reaction scheme:

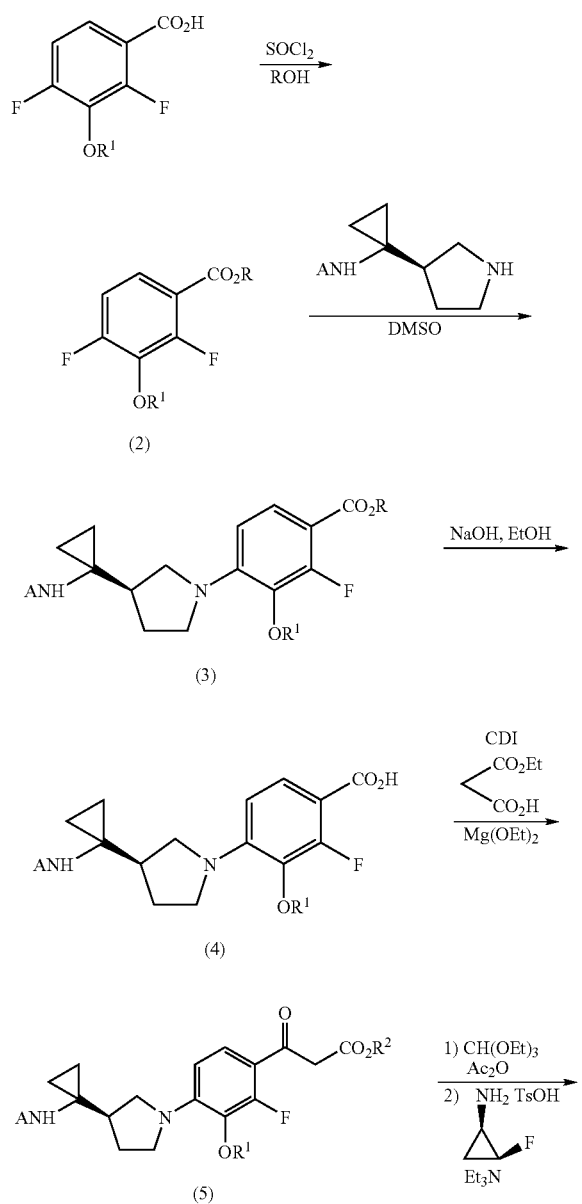

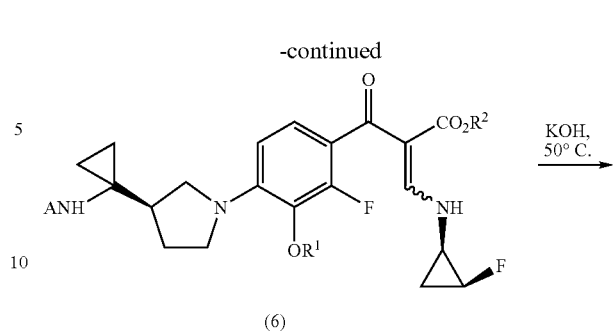

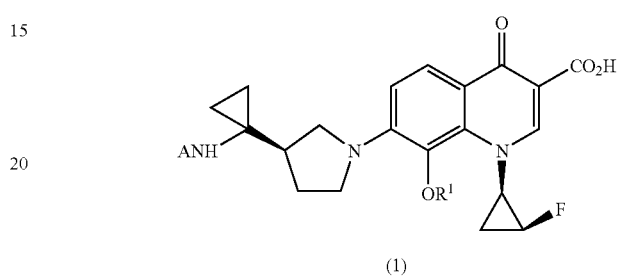

wherein, R, $R^1$ and $R^2$ represent each independently a lower alkyl group, and A represents an amino-protecting group.

Thus, according to the present invention, there is provided a process for producing a compound represented by formula (1):

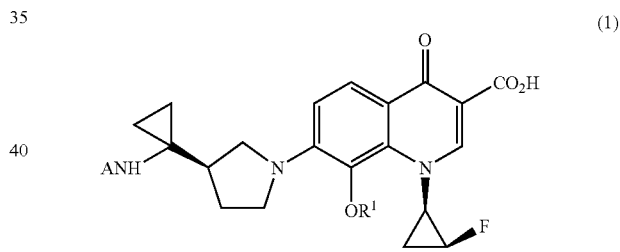

wherein $R^1$ represents a lower alkyl group and A represents an amino-protecting group which comprises treating a compound represented by formula (6):

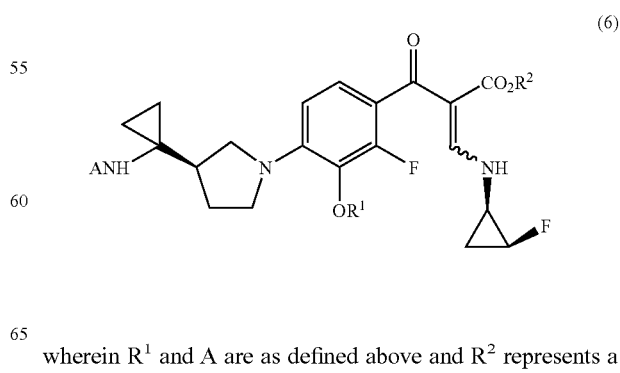

wherein $R^1$ and A are as defined above and $R^2$ represents a lower alkyl group with a base in a water-containing solvent.

The compound represented by formula (6) can be prepared by reacting a compound represented by formula (5):

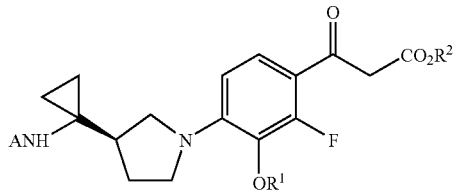

(5)

wherein $R^1$, $R^2$ and A are as defined above with an ortho ester and then with (1R,2S)-2-fluorocyclopropylamine or a salt thereof.

The compound represented by formula (5) can be prepared by converting a compound represented by formula (4):

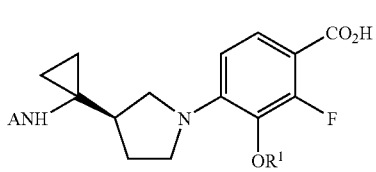

(4)

wherein $R^1$ and A are as defined above to an acid halide with a halogenating agent or to an acylimidazole with a carbonyldiimidazole condensing agent, and then reacting the resultant product with a magnesium salt of a lower alkyl monoester of malonic acid, or, in the presence of a base, with a lower alkyl monoester of malonic acid.

The compound represented by formula (4) can be prepared by hydrolyzing a compound represented by formula (3):

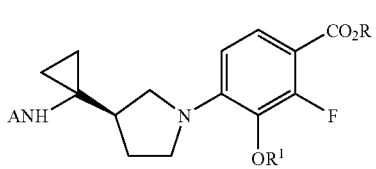

(3)

wherein R represents a lower alkyl group and $R^1$ and A are as defined above.

The compound represented by formula (3) can be prepared by reacting a compound represented by formula (2):

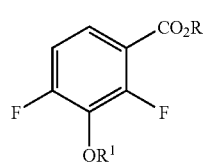

(2)

wherein R and $R^1$ are as defined above with a (3R)-3-(1-aminocyclopropyl)-pyrrolidine represented by the following formula:

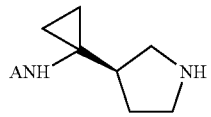

wherein A is as defined above in a solvent which dissolves the compound of formula (2).

The compound represented by formula (2) may be prepared by converting a 2,4-difluoro-3-alkoxybenzoic acid to an acid halide thereof, particularly an acid chloride thereof, by using a halogenating agent such as thionyl chloride or oxalyl chloride, and then adding thereto an alkyl alcohol. In addition, it is possible to obtain the compound by a method usually conducted in which an acid catalyst is used in an alcohol.

EFFECTS OF THE INVENTION

According to the process of the invention, an amino group is position-selectively introduced into a difluorobenzoic acid, whereby expensive (1R,2S)-2-fluorocyclopropylamine tosylate is not necessary at the earlier step of the process for the production of the mother nucleus and thus the production cost is reduced.

MODE FOR CARRYING OUT THE INVENTION $R^1$ in formulae (1) through (6) is preferably a straight or branched lower alkyl group having 1 to 3 carbon atoms such as methyl, ethyl, n-propyl or isopropyl, and is particularly preferably methyl.

$R^2$ in formulae (5) and (6) is preferably a straight or branched lower alkyl group having 1 to 6 carbon atoms such as methyl, ethyl, n-propyl, isopropyl, isopentyl or neopentyl, more preferably methyl or ethyl, and particularly preferably ethyl.

R in formulae (2) and (3) is preferably a straight or branched lower alkyl group having 1 to 6 carbon atoms such as methyl, ethyl, n-propyl, isopropyl, isopentyl or neopentyl, and more preferably methyl or ethyl.

Examples of the amino-protecting group represented by A in formulae (1), (3), (4), (5) and (6) include alkoxycarbonyl groups, aralkyloxycarbonyl groups, acyl groups, aralkyl groups, alkyl groups and substituted silyl groups. Preferred amino-protecting groups include alkoxycarbonyl groups having 2 to 5 carbon atoms and aralkyloxycarbonyl groups, and particularly preferred amino-protecting groups are tert-butoxycarbonyl(Boc) group and benzyloxycarbonyl(Cbz) group.

The compounds of formula (6) are novel compounds. Particularly preferred compounds of formula (6) include one wherein $R^1$ is methyl, $R^2$ is ethyl and A is tert-butoxycarbonyl (Boc).

The compounds of formula (5) are novel compounds. Particularly preferred compounds of formula (5) include one wherein $R^1$ is methyl, $R^2$ is ethyl and A is tert-butoxycarbonyl (Boc).

The compounds of formula (4) are novel compounds. Particularly preferred compounds of formula (4) include one wherein $R^1$ is methyl and A is tert-butoxycarbonyl (Boc).

The compounds of formula (3) are novel compounds. Particularly preferred compounds of formula (3) include those wherein $R^1$ is methyl, R is methyl or ethyl and A is tert-butoxycarbonyl(Boc).

Reaction steps involved in the production of compound (1) which is a precursor of the quinolonecarboxylic acid antibacterial agent starting from a substituted benzoic acid is described in detail.

Substituted Benzoic Acid→Compound (2)

Compound (2) may be prepared by converting a 2,4-difluoro-3-alkoxybenzoic acid to an acid halide, particularly an acid chloride, by using a halogenating agent such as thionyl chloride or oxalyl chloride, and then adding thereto an alkyl alcohol (ROH). Exemplary solvents which may be used in the conversion to the acid halide include ether compounds such as tetrahydrofuran, diethyl ether, dioxane and dimethoxyethane; aromatic compounds such as benzene, toluene and xylene; chlorinated compounds such as methylene chloride and chloroform; ester compounds such as methyl acetate and ethyl acetate; and nitrile compounds such as acetonitrile. The reaction is accomplished at a temperature in the range of −30 to 170° C., preferably 0 to 110° C. The alkyl alcohol to be added may be a primary or secondary alcohol and is particularly preferably ethanol. After completion of the reaction, the product may be obtained according to a commonly used method by adding the reaction mixture which has been optionally concentrated to water, removing the resulting salts, and extracting the filtrate with a water-insoluble organic solvent. The target product can be obtained in a high purity by removing the solvent from the extract. However, when further purification is required, a pure product may be isolated by using column chromatography. The other method for preparing compound (2) includes a usual method which is conducted in the presence of an acid catalyst in an alcohol.

Compound (2)→Compound (3)

Compound (3) may be prepared by reacting compound (2) with 1 to 2 times moles of an amino-protected (3R)-3-(1-aminocyclopropyl)-pyrrolidine, particularly at a stoichiometric ratio (molar ratio) of about 1:1. In this reaction with the pyrrolidine, substitution reaction occurs at ortho-position (2-position) or para-position (4-position) relative to the carboxyl group. Surprisingly, it was found by the present inventors that the position of compound (2) at which the pyrrolidine reacts varies depending on the solvent used and that different compounds having different reaction sites can be selectively obtained by choosing the solvent.

The solvent which may be used in this substitution reaction includes those which dissolve compound (2), such as, for example, ether compounds such as tetrahydrofuran, diethyl ether, dioxane and dimethoxyethan; aromatic compounds such as benzene, toluene, and xylene; chlorinated compounds such as methylene chloride and chloroform; ester compounds such as methyl acetate and ethyl acetate; nitrile compounds such as acetonitrile; N,N-dimethyl acetoformamide, dimethylsulfoxide and ionic liquids. In this process, the polarity of the solvent used is important. In order to effectively obtain compound (3) which is substituted at 4-position, it was revealed that use of a highly polar solvent such as dimethylsulfoxide, N,N-dimethylformamide or an ionic liquid is preferred. Among these highly polar solvents, dimethylsulfoxide is particularly preferred.

The reaction temperature may be in the range of 0 to 170° C., preferably 0 to 100° C.

The reaction is preferably conducted in the presence of a base. The base to be added may be either organic or inorganic, and is preferably a tertiary amine. The amine may be either aromatic or non-aromatic, and is preferably a trialkylamine. Triethylamine may be used. The base is suitably used in an amount of 1 to 5 equivalents, preferably 1 to 2 equivalents based on the amount of compound (2).

After completion of the reaction, the product may be obtained according to a commonly used method by adding the reaction mixture which has been optionally concentrated to water, removing the resulting inorganic salts, and extracting the filtrate with a water-insoluble organic solvent. The target product can be obtained in a high purity by removing the solvent from the extract. However, when further purification is required, a pure product may be isolated by using column chromatography or recrystallization.

This selective amino-substituent introduction reaction found by the present inventors is believed to proceed similarly in the reaction using such cyclic amine compound used in the constitution (introduction) of an amino-substituent into known quinolone compounds. Such cyclic amine compounds include, for example, 5-membered or 6-membered ring cyclic amino compounds and bicyclic amino compounds. Specifically, the cyclic amine compounds include pyrrolidine, 3-aminopyrrolidine, 2-methyl-4-aminopyrrolidine, 3-amino-4-methylpyrrolidine, 7-amino-5-azaspiro[2.4]heptane, 1-amino-5-azaspiro[2.4]heptane, 1-amino-3-azabicyclo[3.1.0]hexane, 3-hydroxypyrrolidine, piperazine, 3-methylpiperazine, 4-methylpiperazine, 3,5-dimethylpiperazine, 2,8-diazabicyclo[4.3.0]nonane and 2-oxa-5,8-azabicyclo[4.3.0]nonane, all of which may be in an optically active form. When amino group or hydroxyl group is additionally included as a substituent on the ring, these groups may be protected.

Compound (3)→Compound (4)

In order to obtain compound (4) from compound (3), the ester of compound (3) may be hydrolyzed. The hydrolysis of this ester may be conducted under conditions usually used and the conditions are not particularly restricted as long as they do not remove the protecting group of the amino group. The hydrolysis of this process is preferably conducted under basic conditions. The base which may be used is preferably an inorganic base and includes sodium hydroxide and potassium hydroxide. The base is suitably used in an amount of 1 to 50 equivalents, preferably 1 to equivalents, based on the amount of compound (3). The reaction may be conducted at a temperature in the range of from room temperature to 300° C., preferably room temperature to about 100° C. The reaction time varies depending on the reaction temperature, and may be approximately from 1 to 48 hours. Usually the reaction completes in 1 to 24 hours. After completion of the reaction, the reaction mixture is acidified and then extracted with a water-insoluble organic solvent or a solid matter is separated from the reaction mixture to obtain compound (4). The acid used for the acidification is not particularly restricted as long as it does not remove amino-protecting group and is preferably citric acid.

Compound (4)→Compound (5)

As a method for producing compound (5), compound (4) is reacted with a halogenating agent such as thionyl chloride preferably at a stoichiometric ratio (molar ratio) of about 1:1 to convert compound (4) to an acid halide, particularly an acid chloride or, alternatively, with a condensing agent such as 1,1'-carbonyldiimidazole preferably in an amount of 1 to 2 moles per mole of compound (4) to convert compound (4) to an acylimidazole, and then magnesium salt of a lower alkyl monoester of malonic acid is added to the product in an amount of 1 to 3 moles per mole of compound (4) to effect reaction. The other method includes a method as disclosed in JP-A-1-100166 wherein a lower alkyl monoester of malonic acid is reacted in the presence of a base such as, for example, an alkyl lithium or sodium hydride in place of the magnesium salt. The term "lower alkyl" herein refers to an alkyl having 1 to 6, preferably 1 to 3 carbon atoms. The solvent which may be used in these reactions includes ether compounds such as tetrahydrofuran, diethyl ether, dioxane and dimethoxyethan; aromatic compounds such as benzene, toluene, and xylene; chlorinated compounds such as methylene chloride and chloroform; ester compounds such as methyl acetate and ethyl acetate; nitrile compounds such as acetonitrile; N,N-dimethylacetoformamide, dimethylsulfoxide and ionic liquids. Among them, ether compounds are particularly preferred. The reaction temperature is in the range of 0 to 170° C., preferably room temperature. After completion of the reaction, the product may be obtained according to a commonly used method by adding the reaction mixture which has been optionally concentrated to water, and extracting the resulting mixture with a water-insoluble organic solvent. The target product can be obtained in a high purity by removing the solvent from the extract. However, when further purification is required, a pure product may be isolated by using column chromatography.

Compound (5)→Compound (6)

Compound (6) may be prepared by reacting compound (5) with an ortho ester such as methyl orthoformate or ethyl orthoformate in acetic anhydride, concentrating the reaction mixture, dissolving the residue and acting thereon (1R,2S)-2-fluorocyclopropylamine or a salt thereof, particularly tosylate thereof. The amount of (1R,2S)-2-fluorocyclopropylamine or the salt thereof used therein per mole of compound (5) is preferably 1 to 1.5 moles, particularly at a stoichiometric ratio (molar ratio) of about 1:1. The solvent which is used therein may be any solvent as long as it does not interfere with the reaction. The reaction temperature is in the range of 0 to 170° C., preferably room temperature. After completion of the reaction, the product may be obtained according to a commonly used method by adding the reaction mixture which has been optionally concentrated to water, and extracting the resulting mixture with a water-insoluble organic solvent. The target product can be obtained in a high purity by removing the solvent from the extract. However, when further purification is required, a pure product may be isolated by using column chromatography.

Compound (6)→Compound (1)

Compound (1) may be obtained by dissolving compound (6) in a water-miscible solvent and treating the solution with a base in the presence of water. Under such condition, a ring-closure reaction to give a quinoline ring and hydrolysis of the ester simultaneously proceed to provide compound (1). The water-miscible solvent is not particularly restricted as long as it does not interfere with the reaction and includes alcohol solvents such as methanol, ethanol and n-propanol; and ether compounds such as dioxane and dimethoxyethane. The base which may be used includes inorganic bases such as sodium hydroxide, potassium hydroxide and lithium hydroxide. The amount of the solvent used is in the range 1 to 100 times by weight, preferably 3 to 10 times by weight the amount of compound (6). The amount of the base may be not less than 2 moles per mole of compound (6). The base is dissolved in water and used in the form of an aqueous solution. The amount of water is adjusted so that the base dissolved in water becomes approximately 0.5 to 10N, preferably approximately 2 to 5N. The reaction may be conducted at a temperature in the range of from room temperature to 300° C., preferably room temperature to 100° C. The reaction time varies depending on the reaction temperature, and is approximately from 1 to 48 hours. Usually the reaction completes in 1 to 5 hours. After completion of the reaction, the reaction mixture is acidified and then extracted with a water-insoluble organic solvent or a solid matter is separated from the reaction mixture to obtain compound (1). The acid used for the acidification is not particularly restricted as long as it does not remove amino-protecting group and is preferably citric acid.

Incidentally, the reaction in this process can be carried out similarly under conditions for a so-called two layer—reaction using a water-immiscible organic solvent, an aqueous base and a phase-transfer catalyst.

By removing the protecting group of the amino group in the resulting compound (1), the quinolonecarboxylic acid derivative represented by formula (1') which is useful as an antibacterial agent is obtained. Deprotection may be carried out under conditions suitable for the protecting group used, and may be effected, for example, by hydrolysis using hydrochloric acid or the like. Incidentally, compound (1') may be isolated as an acid addition salt or hydrate thereof.

EXAMPLES

Processes for production of the compounds of the invention and a quinolonecarboxylic acid derivative using these compounds as an intermediate are specifically described below.

Reference Example 1

Ethyl 2,4-difluoro-3-methoxybenzoate 2,4-Difluoro-3-methoxybenzoic acid (18.8 g) was placed in a reaction vessel and was suspended in 100 ml of toluene added thereto at room temperature. After dropwise addition of 0.5 mL of N,N-dimethylformamide, 14.6 mL of thionyl chloride was added dropwise, and the resulting mixture was heated to 60° C. with stirring. After 7 hours, 50 mL of ethanol was added and an insoluble matter was filtered out. The filtrate was washed with water and saturated brine, and dried with anhydrous sodium sulfate. The solvent was distilled away to give the title compound (21.4 g) as a pale yellow oil.

Example 1

(3R)-3-(1-tert-butoxycarbonylaminocyclopropyl)-pyrrolidine (64 mg, 85% content) was dissolved in a solvent (0.45 mL, see Table 1 below). After adding thereto ethyl 2,4-difluoro-3-methoxybenzoate (45 mg) and triethylamine (0.04 mL), the mixture was stirred at 75° C. After 18 hours, the mixture was allowed to cool, subjected to liquid separation with 10% aqueous citric acid solution, and extracted with AcOEt. An organic layer was dried with anhydrous sodium sulfate. After filtration, the solvent was distilled away. The residue was measured by $^1$H-NMR to determine position-selectivity of amino group to an aromatic compound.

Position-Selectivity of Amino Group

| Solvent | 2-position | 4-position |
|---|---|---|
| Dimethylsulfoxide | 18 | 82 |
| 1-Ethyl-3-methylimidazolium trifluorosulfonate | 20 | 80 |
| N,N-Dimethylformamide | 29 | 71 |
| Acetonitrile | 50 | 50 |
| Tetrahydrofuran | 72 | 28 |
| Ethyl acetate | 80 | 20 |
| Toluene | 90 | 10 |

Ethyl 2-[(3R)-3-(1-tert-butoxycarbonylaminocyclopropyl)-pyrrolidin-1-yl]-4-fluoro-3-methoxybenzoate (a compound introduced at 2-position)

colorless oil; $^1$H-NMR (400 MHz, CDCl$_3$) δ 0.73-0.85 (m, 4H), 1.36 (t, J=6.8 Hz, 3H), 1.42 (s, 9H), 1.66-1.72 (m, 1H), 1.92-2.05 (m, 1H), 2.28-2.43 (m, H), 3.26-3.34 (m, 3H), 3.47-3.53 (m, 1H), 3.82 (s, 3H), 4.10 (q, J=6.8 Hz, 2H), 4.99 (br s, 1H), 6.63 (t, J=9.0 Hz, 1H), 7.19 (dd, J=9.0, 6.4 Hz, 1H).

Ethyl 4-[(3R)-3-(1-tert-butoxycarbonylaminocyclopropyl)-pyrrolidin-1-yl]-2-fluoro-3-methoxybenzoate (a compound introduced at 4-position)

white crystal; $^1$H-NMR (400 MHz, CDCl$_3$) δ 0.76-0.88 (m, 4H), 1.37 (t, J=7.3 Hz, 3H), 1.41 (s, 9H), 1.70-1.79 (m, 1H), 1.95-2.05 (m, 1H), 2.28-2.38 (m, 1H), 3.30-3.38 (m, 1H), 3.45-3.60 (m, 3H), 3.78 (s, 3H), 4.33 (q, J=7.3 Hz, 2H), 4.90 (br s, 1H), 6.31 (d, J=9.0 Hz, 1H), 7.19 (t, J=9.0, 1H).

Example 2

Ethyl 4-[(3R)-3-(1-tert-butoxycarbonylaminocyclopropyl)-pyrrolidin-1-yl]-2-fluoro-3-methoxybenzoate (3R)-3-(1-Tert-butoxycarbonylaminocyclopropyl)-pyrrolidine (4.75 g, 85% content) was dissolved in dimethylsulfoxide (30 mL). After adding thereto ethyl 2,4-difluoro-3-methoxybenzoate (3.2 g) and triethylamine (3.1 mL), the mixture was stirred at 75° C. After 18 hours, the mixture was allowed to cool, incorporated with 10% aqueous citric acid solution, and extracted with AcOEt. An organic layer was dried with anhydrous sodium sulfate and filtered, and then the solvent was distilled away. The resulting residual crystals (6.22 g) (2-position:4-position=17:83) were subjected to chromatography on silica gel (hexane:ethyl acetate=4:1) to give the title compound as white crystals (4.75 g).

Example 3

4-[(3R)-3-(1-tert-butoxycarbonylaminocyclopropyl)-pyrrolidin-1-yl]-2-fluoro-3-methoxybenzoic acid Ethyl 4-[(3R)-3-(1-tert.-butoxycarbonylaminocyclopropyl)-pyrrolidin-1-yl]-2-fluoro-3-methoxybenzoic acid (3.61 g) was dissolved in 28 mL of ethanol, 1N aqueous sodium hydroxide solution (34.5 mL) was added to the solution, and the mixture was heated to 50° C. with stirring. After completion of the reaction, 10% aqueous citric acid solution was added to the mixture followed by extraction with chloroform. An organic layer was dried with anhydrous sodium sulfate and filtered, and then the solvent was distilled away. The title compound was obtained as residual crystals (4.45 g). The crystals were used in the next step without purification.

Example 4

Ethyl {4-[(3R)-3-(1-tert-butoxycarbonylaminocyclopropyl)-pyrrolidin-1-yl]-2-fluoro-3-methoxybenzoyl}acetate A crude product of 4-[(3R)-3-(1-tert-butoxycarbonylaminocyclopropyl)-pyrrolidin-1-yl]-2-fluoro-3-methoxybenzoic acid (2.0 g) was dissolved in 10 mL of tetrahydrofuran at room temperature, and 1,1'-carbonyldiimidazole (0.97 g) was added thereto. The reaction mixture was stirred for 2 hours. In the meantime, 245 mL of tetrahydrofuran was added to monoethyl malonate (1.59 g) while cooling in a water bath. After completion of the dropwise addition, magnesium ethoxide (0.69 g) was added and the reaction mixture was stirred for two hours. After 2 hours, this reaction mixture was added to the former reaction mixture and the resulting reaction mixture was stirred for additional two hours. The reaction mixture was extracted with ethyl acetate after addition of 102 mL of water. An organic layer was washed with an aqueous sodium hydrogen carbonate solution and a saturated brine, dried with anhydrous sodium sulfate and filtered. The filtrate was concentrated under reduced pressure to give 2.6 g of a residual oil. The resulting residual oil was subjected to chromatography on silica gel (hexane:ethyl acetate=2:1) to give the title compound as a pale yellow oil (1.24 g).

pale yellow oil; $^1$H-NMR (400 MHz, CDCl$_3$) δ0.73-0.88 (m, 4H), 1.37 (t, J=6.8 Hz, 3H), 1.41 (s, 9H), 1.66-1.80 (m, 1H), 1.95-2.05 (m, 1H), 2.20-2.44 (m, 1H), 3.25-3.40 (m, 1H), 3.50-3.65 (m, 3H), 3.77 (s, 3H), 3.90 (d, J=3.6 Hz, keto), 4.23 (q, J=6.8 Hz, 2H), 4.92 (br s, 1H), 5.73 (s, enol), 6.31 (d, J=9.0 Hz, 1H), 7.58 (t, J=9.0, 1H), 12.77 (br s, enol).

Example 5

Ethyl (E and Z)-2-{4-[(3R)-3-(1-tert-butoxycarbonylaminocyclopropyl)-pyrrolidin-1-yl]-2-fluoro-3-methoxybenzoyl}-3-[(1R,2S)-2-fluoro-1-cyclopropylamino]acetate Ethyl {4-[(3R)-3-(1-tert-butoxycarbonylaminocyclopropyl)-pyrrolidin-1-yl]-2-fluoro-3-methoxybenzoyl}acetate (0.79 g) was dissolved in acetic anhydride (0.48 mL) and ethyl ortoformate (0.71 mL) at room temperature. The reaction liquid was heated (internal temperature: 120° C.) stirred for 3 hours and then concentrated under reduced pressure. The concentrated residue was dissolved in toluene and toluene was distilled away under reduced pressure. The residue was added eith ethyl acetate (8.0 mL) and was dissolved therein, followed by addition of (1R,2S)-2-fluorocyclopropylamine tosylate (0.46 g) and triethylamine (0.36 mL) in a water bath and stirring for two hours. An insoluble matter in the reaction mixture was distilled out, and the filtrate was washed with a saturated brine and water, and dried with anhydrous sodium sulfate. After filtration, the filtrate was concentrated under reduced pressure to give a crude product (1.11 g) of the title compound which is a mixture of E compound and Z compound as a red oil.

Example 6

7-[(3R)-3-(1-tert-butoxycarbonylaminocyclopropyl)-pyrrolidin-1-yl]-1-[(1R,2S)-2-fluoro-1-cyclopropylamino]-1,4-dihydro-8-methoxy-4-oxoquinoline-3-carboxylic acid A crude product of ethyl (E and Z)-2-{4-[(3R)-3-(1-tert-butoxycarbonylaminocyclopropyl)-pyrrolidin-1-yl]-2-fluoro-3-methoxybenzoyl}-3-[(1R,2S)-2-fluoro-1-cyclopropylamino]acetate (1.08 g) was dissolved in 5 mL of ethanol, added with 10 mL of 3N aqueous potassium hydroxide solution and heated to 50° with stirring. After 2 hours, the reaction mixture was ice-cooled, acidified with 10% aqueous citric acid solution and extracted with chloroform. An organic layer was dried with anhydrous sodium sulfate. After filtration, the solvent was distilled away. The resulting residue (0.89 g) was subjected to column chromatography on silica gel to give the title compound as pale brown crystals.

pale brown crystal; $^1$H-NMR (270 MHz, CDCl$_3$) δ0.68-0.95 (m, 4H), 1.30-1.60 (m, 2H), 1.43 (s, 9H), 1.72-1.90 (m, 1H), 2.05-2.15 (m, 1H), 2.23-2.40 (m, 1H), 3.37-3.71 (m, 4H), 3.53 (s, 3H), 3.80-3.90 (m, 1H), 4.75-5.05 (md, J=51.9 Hz, 1H), 4.98 (brs, 1H), 6.94 (d, J=9.2 Hz, 1H), 8.07 (d, J=9.2 Hz, 1H), 8.66 (d, J=3.1 Hz, 1H), 15.20 (br s, 1H).

The invention claimed is:

1. A process for producing a compound represented by formula (1) from a compound represented by formula (6), comprising:
    treating the compound of formula (6) with a base in a water-containing solvent;
    where formula (1) is:

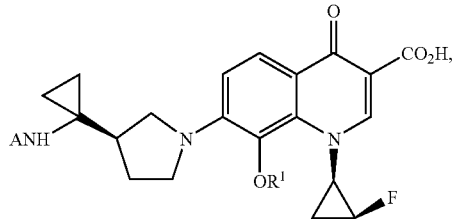

(1)

wherein $R^1$ represents a lower alkyl group and A represents an amino-protecting group; and
where formula (6) is:

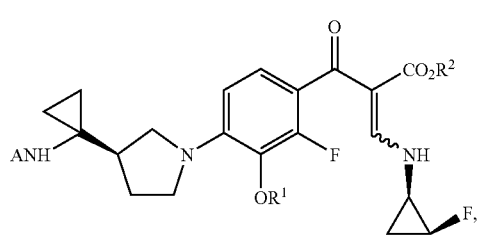

(6)

wherein $R^1$ and A are as defined above and $R^2$ represents a lower alkyl group.

2. The process according to claim 1, further comprising preparing the compound of formula (6) from a compound of formula (5) by reacting the compound of formula (5) with an ortho ester and then with (1R,2S)-2-fluorocyclopropylamine or a salt thereof;
where the compound of formula (5) is:

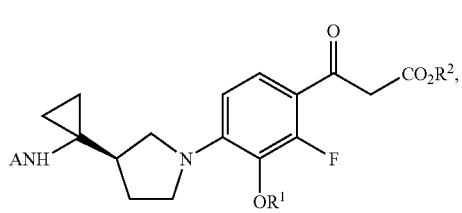

(5)

wherein $R^1$ represents a lower alkyl group, A represents an amino-protecting group, and $R^2$ represents a lower alkyl group.

3. The process according to claim 2, further comprising preparing the compound of formula (5) from a compound of formula (4) by
    converting the compound of formula (4) to an acid halide with a halogenating agent or to an acylimidazole with a carbonyldiimidazole condensing agent, and then reacting the resultant product with a magnesium salt of a lower alkyl monoester of malonic acid; or,
    converting the compound of formula (4) to an acid halide in the presence of a base, with a lower alkyl monoester of malonic acid;
where formula (4) is:

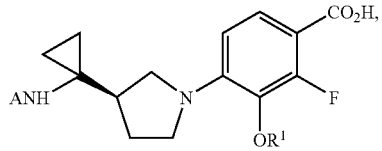

(4)

wherein $R^1$ represents a lower alkyl group, and A represents an amino-protecting group.

4. The process according to claim 3, further comprising preparing the compound of formula (4) by hydrolyzing a compound of formula (3),
    where formula (3) is:

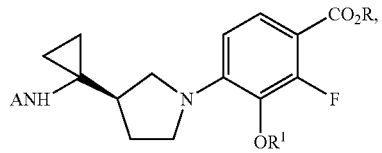

(3)

wherein R represents a lower alkyl group, $R^1$ represents a lower alkyl group, and A represents an amino-protecting group.

5. The process according to claim 4, further comprising preparing the compound of formula (3) by reacting a compound represented by formula (2) in a solvent which dissolves the compound of formula (2):

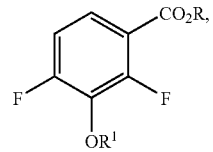

(2)

wherein R represents a lower alkyl group and $R^1$ represents a lower alkyl group;
with a compound represented by the following formula:

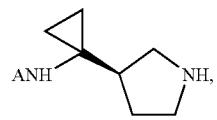

wherein A represents an amino-protecting group.

6. The process according to claim 5, wherein the solvent is a highly polar solvent.

7. The process according to claim 6, wherein the highly polar solvent is one selected from the group consisting of dimethylsulfoxide, N,N-dimethylformamide and ionic liquids.

8. The process according to claim 5, wherein the solvent is dimethylsulfoxide.

* * * * *

UNITED STATES PATENT AND TRADEMARK OFFICE
CERTIFICATE OF CORRECTION

| | | |
|---|---|---|
| PATENT NO. | : 7,626,029 B2 | Page 1 of 1 |
| APPLICATION NO. | : 10/560823 | |
| DATED | : December 1, 2009 | |
| INVENTOR(S) | : Muto et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 978 days.

Signed and Sealed this

Second Day of November, 2010

David J. Kappos
*Director of the United States Patent and Trademark Office*